United States Patent [19]
Craig et al.

[11] Patent Number: 6,063,927
[45] Date of Patent: May 16, 2000

[54] PAROXETINE DERIVATIVES

[75] Inventors: Andrew Simon Craig; Alan David Jones, both of Kent; Deirdre O'Keeffe, Surrey; Neal Ward, East Sussex, all of United Kingdom

[73] Assignee: SmithKline Beecham plc, Brentford, United Kingdom

[21] Appl. No.: 09/299,060

[22] Filed: Apr. 23, 1999

[30] Foreign Application Priority Data

| Jul. 2, 1998 | [GB] | United Kingdom | 9814316 |
| Oct. 6, 1998 | [GB] | United Kingdom | 9821732 |
| Feb. 10, 1999 | [GB] | United Kingdom | 9902935 |

[51] Int. Cl.$^7$ ............... C07D 401/00; C07D 211/06; C07D 211/20

[52] U.S. Cl. ............... 546/197; 546/198; 546/205; 546/206; 546/236

[58] Field of Search ............... 546/197, 198, 546/205, 208, 238

[56] References Cited

U.S. PATENT DOCUMENTS

| 3,912,743 | 10/1975 | Christensen et al. | 260/293.58 |
| 4,007,196 | 2/1977 | Christensen et al. | 260/293.58 |
| 4,585,777 | 4/1986 | Lassen et al. | 514/317 |
| 4,721,723 | 1/1988 | Barnes et al. | 514/321 |
| 4,902,801 | 2/1990 | Faruk et al. | 546/220 |
| 4,985,446 | 1/1991 | Drejer et al. | 514/321 |
| 5,258,517 | 11/1993 | Zepp et al. | 546/240 |
| 5,371,092 | 12/1994 | Johnson | 514/321 |
| 5,639,601 | 6/1997 | Saeki et al. | 435/5 |
| 5,668,134 | 9/1997 | Klimstra et al. | 514/254 |
| 5,672,609 | 9/1997 | Bryant et al. | 514/318 |
| 5,874,447 | 2/1999 | Benneker et al. | 514/321 |

FOREIGN PATENT DOCUMENTS

| 2143070 | 8/1995 | Canada | A61K 47/30 |
| 2187128 | 4/1998 | Canada | C07D 405/12 |
| 0 188 081 A2 | 7/1986 | European Pat. Off. | A61K 31/445 |
| 0 190 496 A2 | 8/1986 | European Pat. Off. | C07D 211/22 |
| 0 219 934 A1 | 4/1987 | European Pat. Off. | C07D 211/36 |
| 0 223 334 A1 | 5/1987 | European Pat. Off. | C07D 211/22 |
| 0 223 403 A2 | 5/1987 | European Pat. Off. | C07D 405/12 |
| 0 266 574 A2 | 5/1988 | European Pat. Off. | C07D 211/22 |
| 0 269 383 A2 | 6/1988 | European Pat. Off. | A61K 31/495 |
| 0 300 617 A1 | 1/1989 | European Pat. Off. | C07D 211/22 |
| 0 374 674 A2 | 6/1990 | European Pat. Off. | C07D 211/20 |
| 0 374 675 A2 | 6/1990 | European Pat. Off. | C07D 211/90 |
| 0 600 714 A1 | 6/1994 | European Pat. Off. | C07C 69/70 |
| 0 714 663 A2 | 6/1996 | European Pat. Off. | A61K 45/06 |
| 0 802 185 A1 | 10/1997 | European Pat. Off. | C07D 211/22 |
| 0 810 224 A1 | 12/1997 | European Pat. Off. | C07D 405/12 |
| 0 810 225 A1 | 12/1997 | European Pat. Off. | C07D 405/12 |
| 0 812 827 A1 | 12/1997 | European Pat. Off. | C07D 211/22 |
| 99678 | 4/1925 | Germany . | |
| 2 404 113 | 8/1974 | Germany | C07D 29/12 |
| 196 03 797 A1 | 8/1996 | Germany | C07D 405/12 |
| 179187 | 1/1974 | Netherlands | A61K 31/445 |
| 1422263 | 1/1976 | United Kingdom | C07D 211/22 |
| 2297550 | 8/1996 | United Kingdom | C07D 405/12 |
| WO 95/09281 | 4/1975 | WIPO | E02F 3/28 |
| WO 93/22284 | 11/1993 | WIPO | C07D 211/90 |
| WO 94/03428 | 2/1994 | WIPO | C07D 211/22 |
| WO 95/15155 | 6/1995 | WIPO | A61K 9/16 |
| WO 95/20964 | 8/1995 | WIPO | A61K 31/445 |
| WO 96/24595 | 8/1996 | WIPO | C07D 405/12 |
| WO 96/31197 | 10/1996 | WIPO | A61K 9/48 |
| WO 96/36636 | 11/1996 | WIPO | C07D 405/12 |
| WO 97/03670 | 2/1997 | WIPO | A61K 31/445 |
| WO 97/16448 | 5/1997 | WIPO | C07D 405/12 |
| WO 97/18798 | 5/1997 | WIPO | A61K 9/16 |
| WO 97/24323 | 7/1997 | WIPO | C07D 211/22 |
| WO 97/31915 | 9/1997 | WIPO | C07D 405/12 |
| WO 98/01424 | 1/1998 | WIPO | C07D 211/22 |

*Primary Examiner*—John Kight
*Assistant Examiner*—Raymond Covington
*Attorney, Agent, or Firm*—Wayne J. Dustman; William T. King; Charles M. Kinzig

[57] ABSTRACT

Piperidine compounds, processes for preparing them, pharmaceutical compositions comprising them and their use in therapy are disclosed.

4 Claims, No Drawings

PAROXETINE DERIVATIVES

The present invention relates to a novel compound, to processes for preparing it, pharmaceutical compositions comprising it and to its use in treating medical disorders.

Pharmaceutical products with antidepressant and anti-Parkinson properties are described in U.S. Pat. No. 3,912, 743 and U.S. Pat. No. 4,007,196. An especially important compound among those disclosed is paroxetine, the (-)trans isomer of 4-(4'-fluorophenyl)-3-(3',4'-methylenedioxy-phenoxymethyl)-piperdine. This compound is used in therapy as the hydrochloride salt for the treatment and prophylaxis of inter alia depression, obsessive compulsive disorder (OCD) and panic.

We have now surprisingly discovered a novel salt of paroxetine which may be used as an alternative to the currently marketed hydrochloride, or as an intermediate in the preparation of the hydrochloride.

According to the present invention there is provided paroxetine methanesulfonate as a novel compound.

In one aspect the novel salt of this invention is provided in non-crystalline form, which may be a solid or oil. The oil is preferably absorbed on a solid carrier, especially a carrier that is usable as a component of a pharmaceutical composition.

In another aspect the novel salt of this invention is provided in crystalline form. When the crystalline form exists as more than one polymorph, each polymorph forms another aspect of this invention.

The paroxetine methanesulfonate salt may be obtained as a solvate; any such solvate forms a further aspect of this invention.

In a further aspect the present invention provides a process for the preparation of a paroxetine methanesulfonate by precipitation from a solution of a paroxetine methanesulfonate, spray drying or freeze drying a solution of a paroxetine methanesulfonate, evaporating a solution of a paroxetine methanesulfonate to a glass, or by vacuum drying of oils of a paroxetine methanesulfonate, or solidification of melts of a paroxetine methanesulfonate.

Preferably such process provides crystalline paroxetine methanesulfonate by crystallization or re-crystallization from a solution of a paroxetine methanesulfonate, and especially on a commercial scale in a reproducible manner.

Paroxetine methanesulfonate may be prepared by chemical modification of a precursor methanesulfonate salt. Suitable precursors are those which may be converted to the methanesulfonate salt by hydrogenation. For example, the N-benzyl derivative of paroxetine methanesulfonate in a suitable solvent (such as a $C_{1-4}$alkanol) may be hydrogenated using a catalyst such as palladium on charcoal to generate a solution of paroxetine methanesulfonate.

Alternatively paroxetine methanesulfonate may be prepared by treating paroxetine free base or a labile derivative thereof with methanesulfonic acid or a labile derivative thereof. For example paroxetine methanesulfonate may be prepared by contacting stoichiometric amounts of the acid and paroxetine base, alternatively an excess of the acid may be used. Preferably the base is in solution and the methanesulfonic acid is used as a solid, liquid, or as a solution, for example in water, ethers, or lower alcohols such as methanol, ethanol, and propan-2-ol, or a mixture of solvents. There is no need for a pure form of paroxetine base to be used as a starting material in the preparation of the methanesulfonate salt.

The term 'labile derivative thereof' used herein with reference to paroxetine refers to derivatives of paroxetine which under the conditions of the reaction with methanesulfonic acid or a labile derivative thereof form the paroxetine methanesulfonate salt. Such labile derivatives include without limitation a salt of paroxetine with an organic acid, particularly with acids weaker than methanesulfonic acid, or labile N-protected forms of paroxetine e.g. N-trimethyl silyl or N-tert-butyloxycarbonyl. Examples of such salts of paroxetine, particularly with weaker acids are salts of paroxetine with organic carboxylic acids, which may be saturated or unsaturated $C_{1-10}$mono-, di-, or tri-carboxylic acids or hydroxy substituted such carboxylic acids, such as tartaric, and especially acetic acid, or maleic acid. Polymorphic forms of such salts, e.g. paroxetine maleate form A or B, may be used. Use of another salt of paroxetine as a starting material is suitable for preparation of the crystalline salt or, if a volatile acid such as acetic acid is used, non-crystalline salts by methods that involve evaporation (such as freeze-drying and spray-drying).

With reference to methanesulfonic acid the term 'labile derivative thereof' refers to derivatives of methanesulfonic acid which under the conditions of reaction with paroxetine or a labile derivative thereof form paroxetine methanesulfonate salt. Such labile derivatives include without limitation salts thereof, especially a soluble salt, e.g. an ammonium or an amine salt thereof (e.g. ethylamine or diethylamine), or immobilized amine salts e.g. a resin.

The paroxetine base may be provided as prepared according to the procedures generally outlined in U.S. Pat. No 4,007,196 and EP-B-0223403, the contents of which are included herein by way of reference. An advantage of the present invention is that paroxetine solutions prepared by a wide variety of synthetic routes may be incorporated into an efficient manufacturing process for paroxetine methanesulfonate.

The paroxetine base may be provided in situ from a preceding reaction step in which the paroxetine base, or a labile derivative thereof, has been formed, e.g. present in the solvent medium in which it has been so formed. Preceding reaction steps leading to the formation of a solution of paroxetine or a labile derivative thereof are generally deprotection reactions, part of a deprotection sequence, or a coupling reaction in the absence of a protecting group. Examples of suitable protecting groups will be apparent to those skilled in the art and include without limitation:

$C_{1-5}$ alkyl and $C_{1-5}$alkylaryl, allyl, phenacyl, quaternary ammonium; carbamates, such as methyl carbamate, diisopropylmethyl carbamate, 2,2,2-trichloroethyl carbamate, benzyl carbamate, (optionally substituted with, for example, $C_{1-5}$ alkyl, nitro, $C_{1-5}$alkyloxy, halogen, cyano), vinyl carbamate, allyl carbamate; N-benzyl derivatives (optionally substituted with, for example, $C_{1-5}$ alkyl, nitro, $C_{1-5}$alkyloxy, halogen, cyano); amides, such as formyl, acetyl, acetoacetyl, benzoyl (optionally substituted with, for example, $C_{1-5}$ alkyl, nitro, $C_{1-5}$alkyloxy, halogen, cyano); acetal derivatives, such as methoxymethyl, pivaloyloxymethyl; nitroso derivatives; silyl, such as trimethylsilyl, tert-butyldimethylsilyl, dimethylthexylsilyl; Sulfur acid derived groups, such as benzenesulfenyl, benzenesulfonyl (optionally substituted with, for example, $C_{1-5}$ alkyl, nitro, $C_{1-5}$alkyloxy, halogen, cyano).

An example of such a preceding step involves hydrolysis of a carbamate precursor (for example, the N-phenoxycarbonyl derivative of paroxetine) in a suitable solvent (such as toluene) using a base such as an alkali metal hydroxide, and provides paroxetine base in solution, for example in toluene. Alternatively the deprotection and salt conversion steps may be combined in a one step process, for example by reacting directly an acid labile paroxetine precursor (e.g. an acid-labile carbamate such as the N-tertbutyloxycarbonyl derivative of paroxetine), with methanesulfonic acid in a suitable solvent (such as propan-2-ol, dichloromethane, dioxane or mixtures thereof). Another example is that disclosed in WO98/01424, the contents of which are included herein by way of reference especially insofar as they relate to deprotection, in which hydrogenation in the presence of a catalyst such as platinum or palladium e.g. deposited on carbon is used to remove a benzyl or substituted, e.g. $C_{1-5}$ alkyl or $C_{1-5}$ alkoxy substituted benzyl group. This reaction may for example take place in water, particularly under acid conditions, or in an organic solvent such as an alcohol, for example a $C_{1-5}$ alkanol which may be straight or branched chain e.g. ethanol or 2-propanol, or a medium containing such an alcohol, and so provides paroxetine or a labile derivative thereof in solution.

The paroxetine base or labile derivative thereof may be formed by evaporation of a solvent or solvent mixture in which the base or labile derivative is solubilized. Such a solvent or solvent mixture may for example be a solvent or solvent mixture medium in which paroxetine has been formed in situ e.g. in a preceding reaction step in the medium. The paroxetine base may be produced in an organic solvent or mixture such as those discussed herein, such as toluene or a medium containing toluene, which is then evaporated to leave a residue e.g. an oil, oily or solid or semi-solid residue. The unpurified paroxetine residue may be used in the preparation of paroxetine methanesulfonate. Alternatively the residue may be resolubilised in a suitable solvent such as a medium comprising an alcohol e.g. as discussed above, suitably propan-2-ol. The solvent may be heated and optionally agitated in order to effect complete dissolution of the residue.

In addition to the above-mentioned solvents, most commonly used solvents are suitable for mobilising, e.g. dissolving or suspending, paroxetine base, for example aromatic hydrocarbon type solvents such as alkylbenzenes e.g. toluene, xylene; alcohols such as $C_{1-8}$ alkanols which may be straight or branched chain e.g. methanol, ethanol, propan-2-ol; esters such as $C_{1-5}$ alkanoate esters such as ethyl acetate; ketones e.g. di-$C_{1-5}$ alkyl ketones such as acetone and butanone; amides such as $C_{1-5}$ alkyl substituted acetamides e.g. dimethyl acetamide; heterocyclic amines e.g. pyridine; halogenated hydrocarbons such as fluoro and/or chloro $C_{1-10}$ alkanes e.g. dichloromethane; nitriles such as $C_{1-10}$ alkyl nitriles e.g. acetonitrile, and ethers e.g. di-$C_{1-5}$ alkyl ethers and cyclic ethers such as tetrahydrofuran and diethyl ether.

In particular the following solvents are suitable for mobilising paroxetine free base: toluene, alcohols such as methanol, ethanol, propan-2-ol, esters such as ethyl acetate, ketones such as acetone and butanone, halogenated hydrocarbons such as dichloromethane, nitriles for example acetonitrile, and ethers such as tetrahydrofuran and diethyl ether.

Suitably mixtures of solvents may also be used e.g. mixtures of the abovementioned solvents. The paroxetine base may be provided in solution in one solvent and then the solution diluted with another solvent, miscible with the first solvent. The second solvent may be added to a solution of the paroxetine base or alternatively the solution of paroxetine base in a first solvent may be added to the second solvent, in both cases optionally with stirring in the first solvent. The mixing of the paroxetine solution and a second solvent may occur at any convenient working temperature between e.g. $-20°$ C. and the boiling point of the solvent, preferably between 15 to 80° C. under an inert atmosphere such as nitrogen.

Methanesulfonic acid is commercially available. It may be used as a neat liquid, or as a solution, for example in water, ethers, or lower alcohols such as methanol, ethanol and propan-2-ol, or a mixture of solvents. More generally it may be added as a neat liquid or preferably in solution, for example in water, or a lower alcohol such as a $C_{1-5}$ alkanol e.g. methanol, ethanol, or propan-2-ol; esters such as $C_{1-5}$ alkanoate esters such as ethyl acetate; aromatic hydrocarbon solvents e.g. a $C_{1-5}$ alkylbenzene such as toluene; di-$C_{1-5}$ alkyl ketone such as acetone, butanone, isomethylbutyl ketone, or a mixture of such solvents. The methanesulfonic acid may also be added in the form of labile derivatives as discussed above, such as a soluble salt, for example ammonium methanesulfonate, or the methanesulfonic acid salt of an amine, for example a $C_{1-5}$ alkylamine such as ethylamine or diethylamine.

The concentration of paroxetine base or labile derivative thereof in the paroxetine feedstock is preferably in the range 5 to 80% weight/volume e.g. 5 to 50% weight/volume, more preferably in the range 10 to 50%, particularly 10 to 30%. The concentration of methanesulfonic acid or labile derivative thereof in the acid feedstock, when added in solution, is preferably in the range 0.1 to 7 molar e.g. 0.1 to 3 molar or 0.5 to 1.5 molar, but more preferably between 1 and 5 molar. A high or low concentration of the acid may be added to a low or high concentration, respectively, of the base, preferably a concentrated solution of the acid is added to a dilute solution of the base. Suitably, depending on the solvent(s) used, the concentration of paroxetine methanesulfonate formed may be in the range 2 to 50% weight/volume, typically 5 to 30%. The concentration ranges of the reactants as defined herein are found to facilitate formation in solution and subsequent precipitation of the paroxetine methanesulfonic acid salt in crystallized form.

The reaction of methanesulfonic acid with paroxetine base is exothermic and results in a rise in temperature; typically by between 10 and 25° C., depending upon the concentration of the solution, unless controlled by cooling. Suitably the addition, in either order, is carried out above ambient conditions e.g. above 25° C. such as between 30 and 80° C. preferably above 30° C. such as between 40 and 60° C. and preferably under an inert atmosphere of nitrogen preferably with agitation e.g. stirring. Whilst temperatures above ambient suitably are used, so as to control the subsequent crystallization process and to produce crystals having reproducible properties e.g. of uniform particle size distribution and habit, temperatures in excess of 90° C. are preferably avoided since degradation occurs resulting in colouration and oil formation. Optionally seeds may be added to the paroxetine solution prior to the addition of the acid component.

The salt may be isolated in solid form by conventional means from a solution thereof obtained as above. For example, a non-crystalline salt may be prepared by precipitation from solution, spray drying, and freeze drying of solutions, evaporating a solution to a glass, or vacuum drying of oils, or solidification of melts obtained from reaction of the free base and the acid.

Prior to the isolation of the paroxetine methanesulfonate salt, water may be removed by azeotropic distillation to avoid the formation of hydrates or to obtain the product in anhydrous form. In that case, suitable solvents for the solution of the salt are those which form an azeotrope with water such as toluene and propan-2-ol. It should also be appreciated that mixtures of solvents can also be used to aid the azeotropic removal of water.

A crystalline salt may be prepared by various methods such as directly crystallizing the material from a solvent in which the product has limited solubility or by triturating for example with ethers such as diethyl ether or otherwise crystallizing a non-crystalline salt.

A number of solvents may be used for the crystallization process including those that are useful industrially; e.g. paroxetine methanesulfonate may be crystallized from a relatively crude feedstock such as is commonly produced during the final stage of the chemical synthesis of paroxetine. In particular solvent systems which are suitable for preparation of paroxetine methanesulfonates can also be used for recrystallization (including crystallization), for example toluene or lower alcohols followed by precipitation with ether or hexane. Alternatively, paroxetine methanesulfonate may be crystallized or recrystallized by cooling and optionally seeding a hot solution in a suitable solvent such as propan-2-ol. An improved yield of the salt is obtained by evaporation of some or all of the solvent or by crystallization at elevated temperature followed by controlled cooling, preferably in stages. Careful control of precipitation temperature and seeding may be used to improve the reproducibility of the production process and the particle size distribution and form of the product.

One method for preparing crystalline paroxetine methanesulfonate salt from solution comprises forming a supersaturated solution of the salt in a solvent and allowing the crystalline salt to precipitate from solution, for example by maintaining the solution in relatively quiescent conditions, e.g. under gentle stirring or leaving the solution to stand. Seeding of the solution is optional. By selection of a suitable solvent medium and concentration the present invention provides a process in which crystalline paroxetine methanesulfonate precipitates at temperatures above −20° C. e.g. above 0° C. e.g. around ambient conditions of 10 to 25° C. Suitable solvent media for this method comprise $C_{1-5}$ alkyl benzenes such as toluene, alcohols e.g. $C_{1-5}$ alkanols such as 2-propanol, di-$C_{1-5}$ alkyl ketones such as acetone, ethers such as $C_{4-6}$ cyclic ethers such as tetrahydrofuran or mixtures thereof, and in particular mixtures of such alkyl benzenes with such alkanols or ketones e.g. toluene and 2-propanol or toluene-acetone mixtures.

Another method of preparing crystalline paroxetine methanesulfonate salt comprises forming a solution of the salt, for example as defined herein, and subsequently supersaturating the solution for example by evaporation of the solvent and/or the addition of an anti-solvent to precipitate the crystalline salt from solution. An "anti-solvent", as referred to herein, is a medium such as an organic liquid, which is miscible with a solvent for paroxetine methanesulfonate salt but in which the paroxetine methanesulfonate salt is less soluble than in the solvent. Preferably the solubility of paroxetine methanesulfonate salt in the anti-solvent is less than 1 mg/ml, preferably less than 0.2 mg/ml, especially less than 0.1 mg/ml. Examples of anti-solvents include ethers, e.g. di-$C_{1-5}$ alkyl ethers and alkanes, such as $C_{5-10}$ alkanes which may be straight chain, branched chain or cyclic such as hexane. Solvent systems which are suitable for preparation of paroxetine methanesulfonate, e.g. those discussed above, e.g. with reference to the solvent systems used for the deprotection reactions discussed above, can also be used for recrystallization by precipitation with an anti-solvent. A preferred method of preparing crystalline paroxetine methanesulfonate salt comprises cooling and optionally seeding a solution in a suitable solvent in which the paroxetine methanesulfonate salt has a greater solubility at higher temperatures than at lower temperatures so that as the solution cools the solubility at lower temperatures will be exceeded and the paroxetine methanesulfonate salt crystallises out.

Suitably the solubility of the paroxetine methanesulfonate salt at or immediately below the boiling point of the solvent is 5× or more, preferably 10× or more than that at ambient temperatures (e.g. ca. 20° C.) or lower. Suitable solvent systems include alkylbenzenes, e.g. $C_{1-3}$ alkylbenzenes such as toluene, alcohols such as $C_{1-5}$ alkanols such as methanol, ethanol, 2-propanol, and butan-1-ol, ketones such as di-$C_{1-5}$ alkyl ketones such as acetone, methyl ethyl ketone, methylisobutyl ketone, esters such as $C_{1-5}$ alkyl $C_{1-5}$ alkanoates such as methyl acetate, ethyl acetate, propyl acetate, isopropyl acetate, butyl acetate, and ethers such as methyl t-butyl ether and $C_{4-6}$ cyclic ethers such as tetrahydrofuran. Single and mixed solvent systems may be used as the solvent or co-solvent of choice.

The starting temperature of the solution containing the paroxetine methanesulfonate salt to be crystallized may vary depending upon the solubility of the reactants in the solvent system. Suitable temperatures are between minus 20° C. and (+)80° C., although temperatures between (+)10° C. and (+)70° C. are preferred and temperatures above (+)30° C. e.g. between (+)40° and (+)60° C. are most preferred. The solution is cooled to a temperature within the metastable zone in initiate crystallization. Once crystallization is underway, the temperature of the mixture may be reduced steadily or in stages in order to maintain a moderate degree of supersaturation and a controlled crystallization at a high yield. The cooling rate is preferably within the range 0.1 to 5° C./minute and even more preferably is between 0.1 to 2° C. per minute. The final temperature at the end of the crystallization process is preferably around or below ambient e.g. 5 to 25° C. even more preferably 10 to 20° C. Advantageously the methods provided herein do not require low temperatures i.e. less than 0° C. in order to enable the crystallization process. An improved yield and quality of the paroxetine methanesulfonate salt may be obtained by combining two or more of the aforementioned crystallization methods. For example by evaporating some or all the solvent and/or by crystallization at elevated temperature followed by controlled cooling, preferably in stages.

Seeds may be used to initiate, encourage or facilitate crystallization. The seeds may comprise the methanesulfonate salt e.g. in a crude form such as that obtained by evaporation of a solution or other salt such that is substantially isomorphous with the paroxetine methanesulfonate crystals formed. Preferably the seeds are produced from a standard manufacturing run and typically have a purity in the range 96 to 99% or greater.

Inadvertent seeding may occur from the surrounding environment resulting in poorly controlled crystallization. Preferably crystallization is controlled by deliberate seeding at an above ambient temperature and preferably from a solution that is not excessively supersaturated. Seeds may be added at any time before crystallization but preferably immediately before supersaturation of the paroxetine methanesulfonate salt. Careful control of precipitation, temperature and seeding may be used to improve the reproducibility of the production process and the particle size distribution and form of the product.

In further aspects the present invention provides for the use of techniques such as insonation in the preparation of crystalline paroxetine methanesulfonate salt. Insonation and/or vigorous stirring may be used to initiate nucleation for example in addition to the use of anti-solvent(s), cooling, evaporation and/or seeding. Vigorous stirring is particularly useful when the crystallization vessel used has been used previously in the manufacture of the methanesulfonate salt.

The methods provided herein provide crystalline paroxetine methanesulfonate in a sufficiently pure state for its use as a pharmaceutical per se or as a chemical intermediate in the preparation of other paroxetine forms. However the present invention also provides a method for the optional additional purification of paroxetine methanesulfonate by recrystallization. Such a method may also be used to provide a solid state form having a particular desired habit and particle size distribution.

The same solvents and methods for crystallization as herein described can be used for recrystallization. The most commonly used solvents used for recrystallization are aromatic hydrocarbons e.g. toluene; alcohols such as $C_{1-8}$ alkanols which may be straight or branched chain e.g. methanol, ethanol and propan-2-ol; esters such as $C_{1-5}$ alkanoate esters such as ethyl acetate; halogenated hydrocarbons such as fluoro and/or chloro $C_{1-10}$ alkanes e.g. dichloromethane and ketones e.g. acetone and butanone. Mixtures of solvents may also be used e.g. mixtures containing water. A particularly useful solvent, both with respect to its pharmaceutical acceptability and the quality of the resulting paroxetine methanesulfonate is propan-2-ol. Use of certain solvents and/or solvent mixtures e.g. those containing propan-2-ol, avoids problems of oiling, i.e. formation of a soft sticky product. In addition difficulties in stirring and adhesion of product to the container walls as well as problems associated with drying the product are avoided. Typically between 2 and 20 l/kg of solvent may be used for recrystallization on an industrial scale, preferably between 3 and 10 l/kg.

The abovementioned processes for preparing the paroxetine methanesulfonate salt may be carried out in various types of reaction vessels. The crystallisation of paroxetine methanesulfonate salt suitable for use as a pharmaceutical may be carried out in a vessel such as a stirred tank reactor, which may be constructed from glass-lined or stainless steel, fitted with baffles and one or more jackets to control the temperature profile during crystallisation. Alternatively, the crystallisation may be carried out in a specially designed batch crystalliser, in which fine control of the crystallisation conditions can be maintained. Suitable batch crystallisers include draft tube baffled (DTB) crystallisers, double propeller (DP) crystallisers and fluidised bed crystallisers (Oslo cooling crystallisers). Various continuous crystallisers, such as draft tube cooling, direct contact cooling, scraped surface and turbulence crystallisers may also be employed.

Suitably crystallization is carried out in a vessel provided with one or more high intensity ultrasonic horns, for example with titanium alloy resonant horns which enable acoustic energy to be coupled to the crystallizing medium at a frequency of 20 kHz and an amplitude of 12 microns or more, and with a device that modifies the power output according to the acoustic parameters of the load. Insonation may be intermittent, limited to part of the apparatus, or discontinued once sufficient nuclei have been generated.

The solvent wet cake, comprising paroxetine methanesulfonate, recovered from the crystallization and recrystallization processes described herein may be dried so as to give the desired moisture content for the salt form. Drying may be effected by using one or more dryers e.g. a conventional drying oven, a filter dryer or a stirred pan dryer. Suitably the drying temperature may vary from below ambient to 80° C. and a typical drying cycle may take 12–24 hours. Alternative drying methods, e.g. using a microwave oven, may also be used. Advantageously such a method enables more accurate temperature control and drying times may be reduced considerably e.g. a typical drying cycle may take 2–6 hours, depending upon the quantity of material to be dried and the microwave power used.

In a further aspect the present invention provides the paroxetine methanesulfonate salt in a crystalline form having an X-ray powder diffraction pattern identical or substantially identical to that listed under Example 2 or Example 3 below. Suitably the crystalline paroxetine methanesulfonate has inter alia one or more of the following characteristic XRD peaks: 8.3, 10.5, 15.6, 16.3, 17.7, 18.2, 19.8, 20.4 21.5, 22.0, 22.4, 23.8, 24.4, 25.0, 25.3, 25.8, 26.6. 30.0, 30.2, and 31.6±0.2 degrees 2 theta.

In a further aspect the present invention provides the paroxetine methanesulfonate salt in a crystalline form having an infra-red spectrum identical or substantially identical to that listed under Example 2 or Example 3 below. Suitably the crystalline paroxetine methanesulfonate has inter alia one or more of the following characteristic IR peaks: 1603, 1513, 1194, 1045, 946, 830, 776, 601, 554, and 539±4 cm−1.

Crystals of the present invention may have a range of particle sizes. Typically the particle size is distributed over a range. Suitably more than 90% of the particles have a size of 1 to 1000 microns and preferably are within the range 50 to 300 microns, as measured by Low Angle Laser Light Scattering (LALLS) using a Sympatec Helos/Rodos instrument.

Typically methanesulfonate salts produced in the present invention have a melting point greater than 143° C., e.g. having a melting point of 143 to 146° C., preferably within the range from 144 to 148° C., more preferably greater than 144° C., e.g. 145 to 146° C., 147 to 148° C., The paroxetine methanesulfonate salt may be obtain during isolation from solution it becomes associated with the solvent in which it is dissolved. Any such solvate forms a further aspect of this invention e.g. crystallization of paroxetine methanesulfonate from acetonitrile results in the formation of a 1:1 solvate.

Solvates may be returned to the unsolvated paroxetine methanesulfonate salt by heating, for example by oven-drying, or by treatment with a displacement solvent which does not form a solvate.

Individual polymorphs are preferably crystallized directly from a solution of the paroxetine methanesulfonate salt, although recrystallizing a solution of one polymorph using seeds of another polymorph may also be carried out.

The compounds of this invention may be used to treat and prevent the following disorders:

| | |
|---|---|
| Alcoholism | Anxiety |
| Depression | Obsessive Compulsive Disorder |
| Panic Disorder | Chronic Pain |
| Obesity | Senile Dementia |
| Migraine | Bulimia |
| Anorexia | Social Phobia |
| Pre-Menstrual Syndrome (PMS) | Adolescent Depression |
| Trichotillomania | Dysthymia |
| Substance Abuse | |

These disorders are herein after referred to as "the Disorders".

The present invention further provides a method for treating and/or preventing any one or more of the Disorders by administering an effective and/or prophylactic amount of a salt of the invention to a sufferer in need thereof The present invention further provides a pharmaceutical composition for use in the treatment and/or prevention of the Disorders which comprises an admixture of a salt of the invention with a pharmaceutically acceptable carrier.

The present invention also provides the use of a salt of the invention for treating and/or preventing the Disorders.

The present invention also provides the use of a salt of the invention in the manufacture of a medicament for treating and/or preventing the Disorders.

Most suitably the present invention is applied to the treatment of depression OCD and panic.

The compositions of this invention are usually adapted for oral administration, but formulations for dissolution for parental administration are also within the scope of this invention.

The composition is usually presented as a unit dose composition containing from 1 to 200 mg of active ingredient calculated on a free base basis, more usually from 5 to 100 mg, for example 10 to 50 mg such as 10, 12.5, 15, 20, 25, 30 or 40 mg by a human patient. Most preferably unit doses contain 20 mg of active ingredient calculated on a free base basis. Such a composition is normally taken from 1 to 6 times daily for example 2, 3 or 4 times daily so that the total amount of active agent administered is within the range 5 to 400 mg of active ingredient calculated on a free base basis. Thus a suitable daily dose is from 0.05 to 6 mg/kg, more preferably 0.14 to 0.86 mg/kg. Most preferably the unit dose is taken once a day.

Preferred unit dosage forms include tablets or capsules, especially a modified oval or pentagonal shaped tablet.

The compositions of this invention may be formulated by conventional methods of admixture such as blending, filling and compressing.

Suitable carriers for use in this invention include a diluent, a binder, a disintegrant, a colouring agent. a flavouring agent and/or preservative. These agents may be utilized in conventional manner, for example in a manner similar to that already used for marketed anti-depressant agents.

Suitably the carrier for use in this invention comprises a disintegrant.

Such disintegrant will be present in an effective amount, for example up to 30% by weight of the composition, to ensure disintegration of the composition in vivo.

Suitably the carrier for use in this invention comprises a binder.

Suitably the carrier for use in this invention comprises a colouring agent.

Such colouring agent may be used to colour a tablet coating. Commonly used colouring agents arc 'lakes' which are largely water insoluble forms of synthetic water soluble dyes. They are prepared by adsorbing a sodium or potassium salt of a dye onto a very fine substrate of hydrated alumina, followed by treatment with a further soluble aluminium salt. The lake is then purified and dried. Examples of suitable lakes include yellow coloured lakes such as sunset yellow and quinoline yellow; red coloured lakes e.g. helindone pink; blue coloured lakes e.g. indigotine; or mixtures thereof. Suitably compositions of the present invention comprise an amount of colouring agent sufficient to colour the dosage form e.g. 0.001–1.0% w/w.

Suitably the carrier for use in this invention comprises a flavouring agent.

Suitably the carrier for use in this invention comprises a preservative.

Specific examples of pharmaceutical compositions include those described EP-B-0223403, and U.S. Pat. No. 4,007,196 in which the products of the present invention may be used as the active ingredients.

In a further aspect the present invention provides a pack comprising a pharmaceutical composition of the present invention.

This invention provides the use of paroxetine methanesulfonate as an intermediate in the preparation of the hydrochloride and also provides a process which comprises converting paroxetine methanesulfonate into paroxetine hydrochloride.

The following Examples illustrate the present invention. All melting points quoted were determined using conventional melting point apparatus such as a Bushi apparatus, and were computed from a calibrated instrument.

EXAMPLE 1

A solution of paroxetine base in toluene (2.1 g in 5 ml) was mixed with a solution of methanesulfonic acid (0.61 g) in toluene (15 ml), and stirred at 50° C. for 20 minutes. The solvent was removed in vacuo, and the residue triturated with diethyl ether (50 ml) to produce a crystalline solid, which was filtered, washed with diethyl ether (15 ml) and dried in a vacuum desiccator.

Yield 2.62 g.

EXAMPLE 2

A solution of paroxetine base in toluene (42 g in 100 ml) was added to a solution of methanesulfonic acid (12.2 g) in toluene (300 ml). The solution was stirred for 30 minutes at 50° C., then the solvent was removed by evaporation at reduced pressure. The residue was triturated with diethyl ether (300 ml), and stirred at approximately 20° C. to produce a white crystalline solid which was filtered, washed with diethyl ether (2×100 ml) and dried in a vacuum desiccator.

Yield 54.55 g. m. p. 143–146° C.

IR nujol mull:

Bands at inter alia 1603, 1513, 1462, 1377, 1194, 1045, 946, 830, 776, 601, 554, 539 cm$^{-1}$.

The same characterising IR bands are found when using KBr discs except for the 1462 and 1377 bands which are characteristic of nujol.

X-ray powder diffractogram major peaks (CuK$_{2a}$):

| Angle [°2θ] | Rel. Int [%] |
|---|---|
| 8.3 | 38.5 |
| 10.5 | 11.3 |
| 15.6 | 10.9 |
| 16.3 | 13.8 |
| 17.7 | 43.6 |
| 18.2 | 92.8 |
| 19.8 | 11.4 |
| 20.4 | 23.4 |
| 21.5 | 50.2 |
| 22.0 | 70.4 |
| 22.4 | 10.7 |
| 23.8 | 22.4 |
| 24.4 | 100.0 |
| 25.0 | 27.8 |
| 25.3 | 17.1 |
| 25.8 | 25.2 |
| 26.6 | 22.5 |
| 30.0 | 11.1 |
| 30.2 | 13.6 |
| 31.6 | 10.7 |

EXAMPLE 3

A mixture of methanesulfonic acid (13.7 g) dissolved in toluene (400 ml) and a solution of paroxetine base (47.0 g)

in toluene (100 ml), obtained directly from the base hydrolysis of the N-phenoxycarbonyl intermediate, was evaporated at reduced pressure at 18° C. The resulting white, non-crystalline solid was triturated with diethyl ether to give paroxetine methanesulfonate as a white crystalline solid. The product was collected by filtration and dried overnight in a vacuum desiccator over phosphoric oxide. Yield=56.8 g. Proton nuclear magnetic resonance spectroscopy showed that the molar ratio of paroxetine to methanesulfonic acid was 1:1.

IR (nujol mull): Bands at, inter alia, 1638, 1614, 1603, 1513, 1499, 1399, 1377, 1278, 1254, 1194, 1163, 1145, 1132, 1103, 1095, 1046, 1034, 1010, 946, 927, 916, 870, 845, 830, 822, 787, 776, 766, 721, 601, 572, 554, 539, 529, 514 cm$^{-1}$.

IR (attenuated total reflection): Bands at, inter alia, 1637, 1614, 1603, 1512, 1498, 1469, 1399, 1277, 1254, 1192, 1163, 1145, 1132, 1094, 1076, 1045, 1032, 946, 926, 916, 870, 845, 829, 822, 809, 787, 775, 766, 721, 600, 572, 554 cm$^{-1}$.

X-ray diffractogram major peaks (Cu K$_{2\alpha}$):

| Angle [°2θ] | Rel. Int [%] |
|---|---|
| 6.7 | 8.5 |
| 8.2 | 46.5 |
| 10.4 | 9.9 |
| 10.9 | 5.5 |
| 13.9 | 8.6 |
| 14.7 | 7.1 |
| 15.6 | 8.2 |
| 16.3 | 15.8 |
| 17.7 | 39.6 |
| 18.2 | 93.9 |
| 19.8 | 9.0 |
| 20.5 | 23.0 |
| 21.5 | 50.2 |
| 21.9 | 83.7 |
| 22.4 | 11.8 |
| 23.8 | 23.0 |
| 24.3 | 100.0 |
| 24.9 | 29.4 |
| 25.3 | 17.5 |
| 25.7 | 26.0 |
| 26.5 | 21.9 |
| 27.3 | 5.3 |
| 27.8 | 11.1 |
| 28.3 | 5.9 |
| 28.6 | 7.6 |
| 29.0 | 8.0 |
| 29.6 | 8.6 |
| 30.0 | 12.5 |
| 30.2 | 14.4 |
| 30.6 | 10.2 |
| 31.5 | 13.7 |
| 32.4 | 7.5 |
| 33.1 | 10.8 |
| 34.5 | 7.1 |
| 34.4 | 6.5 |

EXAMPLE 4

A round bottomed flask was charged with a solution of paroxetine base (23.5 g) in toluene (50 ml), obtained directly from the base hydrolysis of the N-phenoxycarbonyl intermediate, and the toluene was removed by evaporation at reduced pressure. The residue was dissolved in propan-2-ol (150 ml) with gentle warming, and the solution cooled to 18° C. Methanesulfonic acid (6.86 g) was added and the solution stirred at 18° C. Seeds of crystalline paroxetine methanesulfonate were added, and the mixture was ultrasonicated. After about 1 minute, a dense crystalline precipitate formed, which was allowed to stand for 20 minutes. The product, paroxetine methanesulfonate, was collected by filtration and dried over phosphoric oxide in a vacuum desiccator.

Yield 29.8 g Melting point=145–146° C.

The infra-red spectrum and X-ray powder diffractogram were the same as in Example 3.

IR (KBr disc): Bands at, inter alia, 3006, 1638, 1614, 1604, 1513, 1499, 1469, 1422, 1399, 1358, 1336, 1278, 1194, 1163, 1144, 1132, 1095, 1091, 1045, 1034, 946, 927, 916, 870, 830, 822, 787, 776, 766, 601, 572, 554, 539, 529, 514 cm–1.

EXAMPLE 5

A solution of paroxetine base (4.7 g) in toluene (40 ml), obtained directly from the base hydrolysis of the N-phenoxycarbonyl intermediate, was stirred at 18° C. and methanesulfonic acid (0.93 ml) was added dropwise. Seeds of crystalline paroxetine methanesulfonate were added and the mixture was treated with ultrasound. After a short time, crystalline paroxetine methanesulfonate precipitated from solution, and the mixture was left to stand overnight. The product was collected by filtration and dried under vacuum.

EXAMPLE 6

Unpurified paroxetine base (4.7 g) was dissolved in tetrahydrofuran (10 ml) with gentle warming. Methanesulfonic acid (1.37 g) was added dropwise to the stirred solution and the clear mixture cooled to 18° C. After five minutes, seeds of crystalline paroxetine methanesulfonate were added, and the mixture was insonated. Crystalline paroxetine methanesulfonate precipitated from solution, and the mixture was left to stand overnight. The product was collected by filtration and dried under vacuum.

EXAMPLE 7

Unpurified paroxetine base (4.7 g) was dissolved in butanone (50 ml), and methanesulfonic acid (1.37 g) was added dropwise. Seeds of crystalline paroxetine methanesulfonate were added to the stirred solution, and the clear mixture was insonated. After a short while, crystalline paroxetine methanesulfonate precipitated from solution, and the mixture was left to stand overnight. The product was collected by filtration and dried under vacuum.

EXAMPLE 8

Propan-2-ol (40 ml) was added at 19° C. under a nitrogen atmosphere to a stirred solution of paroxetine base (8.0 g) in toluene (20 ml), obtained directly from the base hydrolysis of the N-phenoxycarbonyl intermediate. Methanesulfonic acid (2.45 g) was added to the solution and stirring was continued for one hour. A white crystalline solid formed and was collected by filtration, washed with propan-2-ol (15 ml) and dried at 40° C. under vacuum for one hour to produce crystalline paroxetine methanesulfonate, 8.8 g (85%).

IR (nujol mull): bands at inter alia 1638, 1603, 1513, 1377, 1278, 1194, 1093, 1045, 1033, 946, 927, 830, 786, 776, 722, 601, 554, 540 cm$^{-1}$.

EXAMPLE 9

Acetone (40 ml) was added at 19° C. under a nitrogen atmosphere to a stirred solution of paroxetine base (8.0 g) in toluene (20 ml), obtained directly from the base hydrolysis of the N-phenoxycarbonyl intermediate. Methanesulfonic acid (2.45 g) was added to the solution and stirring was continued for one hour. The white crystalline solid which separated from the solution was collected by filtration, washed with acetone (15 ml) and dried at 40° C. under vacuum for one hour to produce crystalline paroxetine methanesulfonate, 9.7 g (94%).

IR (nujol mull): bands at inter alia 1638, 1603, 1513, 1377, 1278, 1194, 1093, 1046, 1033, 946, 927, 830, 786, 776, 722, 601, 554, 540 cm$^{-1}$.

EXAMPLE 10

Methanesulfonic acid (2.45 g) was added at 19° C. under a nitrogen atmosphere to a solution of paroxetine base (8.0 g) in toluene (50 ml), obtained directly from the base hydrolysis of the N-phenoxycarbonyl intermediate, and the mixture was stirred for one hour. A white crystalline solid separated from the solution and was collected by filtration, washed with toluene (10 ml) and dried at 40° C. under vacuum for one hour to produce paroxetine methanesulfonate, 9.6 g (93%).

IR (nujol mull): bands at inter alia 1638, 1603, 1513, 1377, 1278, 1194, 1094. 1046, 1033, 946, 927, 830, 786, 776, 722, 601, 554, 540 cm$^{-1}$.

EXAMPLE 11

A stirred mixture of N-phenoxycarbonyl paroxetine (19.4 g), potassium hydroxide (17.5 g) and toluene (300 ml) was heated to reflux under a nitrogen atmosphere for 3 hours. The mixture was cooled to room temperature, washed with water (200 ml) and the organic layer separated, dried over magnesium sulphate and concentrated to a total volume of approximately 80 ml. Methanesulfonic acid (4.35 g) was added to the solution and the mixture stirred for one hour. The white crystalline solid which crystallised during this time was collected by filtration, washed with toluene (20 ml) and dried at 40° C. under vacuum for one hour to produce paroxetine methanesulfonate, 16.7 g (91%).

IR (nujol mull): bands at inter alia 1638, 1603, 1513, 1377, 1278, 1194, 1094, 1046, 1033, 946, 927, 830, 786, 776, 722, 601, 554, 540 cm$^{-1}$.

EXAMPLE 12

A round bottomed flask was charged with a solution of paroxetine base (23.5 g) in toluene (50 ml), obtained directly from the base hydrolysis of the N-phenoxycarbonyl intermediate. The toluene was removed in vacuo to produce an oily residue. To this residue was added propan-2-ol (50 ml) and the mixture was warmed to ensure total dissolution of the paroxetine. The temperature of the solution was cooled to 18° C. and methanesulfonic acid (6.86 g) was added, then the solvents were removed at reduced pressure and replaced with fresh propan-2-ol (110 ml). The solution was heated to reflux temperature, cooled to 18° C., and seeded with crystalline paroxetine methanesulfonate. Crystallisation was induced with vigorous stirring and insonation, and the product collected by filtration, and dried over phosphorus pentoxide in a vacuum desiccator to produce paroxetine methanesulfonate as a white crystalline solid.

Melting point=145–146° C.

The infra-red spectrum and X-ray powder diffractogram were the same as in Example 3.

EXAMPLE 13

Paroxetine methanesulfonate (0.7 g) was added to ethanol (2 ml), stirred and heated to reflux temperature to dissolve. The resulting solution was cooled to 18° C. and seeded with crystals of paroxetine methanesulfonate. A white precipitate of needle crystals formed, which was collected by filtration, washed with ethanol and dried in vacuo over phosphorous pentoxide to produce crystalline paroxetine methanesulfonate.

Yield=0.52 g. Melting point: 146–147° C.

EXAMPLE 14

Paroxetine methanesulfonate (0.95 g) was added to acetone (10 ml) and the solution heated to reflux temperature while stirring. The solution was cooled to 18° C. and seeded with crystals of paroxetine methanesulfonate. A white precipitate of needle crystals formed, and was collected by filtration, washed with acetone and dried in vacuo over phosphorous pentoxide to produce crystalline paroxetine methanesulfonate. Yield=0.71 g.

Melting point: 146–148° C.

The infra-red spectrum and X-ray powder diffractogram were the same as in Example 3.

EXAMPLE 15

Paroxetine methanesulfonate (1.06 g) was added to ethyl acetate (70 ml) and the solution was heated to reflux temperature while stirring. The solution was cooled to 18° C. and seeded with crystals of paroxetine methanesulfonate. A white precipitate of large needle crystals (0.4–1 mm in length) formed, and was collected by filtration, washed with ethyl acetate and dried in a vacuum desiccator over phosphorous pentoxide to produce crystalline paroxetine methanesulfonate. Yield=0.92 g.

Melting point: 146–147° C.

The infra-red spectrum and X-ray powder diffractogram were the same as in Example 3.

EXAMPLE 16

Paroxetine methanesulfonate (1.11 g) was added to toluene (4 ml) and the solution was heated to reflux temperature while stirring. The resulting solution was cooled to 18° C. and seeded with crystals of paroxetine methanesulfonate. A white precipitate of needle crystals formed, which was collected by filtration, washed with toluene and dried in a vacuum desiccator over phosphorous pentoxide to produce crystalline paroxetine methanesulfonate.

The infra-red spectrum and X-ray powder diffractogram were the same as in Example 3.

EXAMPLE 17

A toluene solution (1.0 L) containing unpurified paroxetine base (approximately 225 g) was charged to a nitrogen purged reactor and stirred at 20° C. The vessel was seeded with paroxetine methanesulfonate, then a solution of methane sulfonic acid (70 g) in propan-2-ol (0.4 L) was added slowly over a period of 50 minutes. Paroxetine methansulfonate was precipitated as a white crystalline solid during the addition, and the temperature at the end of the addition was 29.6° C. The suspension was stirred for a further 1 hour, during which time the temperature was reduced to 22° C. The product was collected by filtration, washed on the filter with propan-2-ol (2×0.4 L) and dried in a vacuum oven at 40° C. for 24 hours. Yield 230 g.

EXAMPLE 18

Paroxetine methanesulfonate (0.81 g) was added to methyl ethyl ketone (10 ml) and the mixture was heated to reflux temperature while stirring to dissolve, then cooled to 18° C. A white precipitate of needle crystals formed, which was collected by filtration, washed with methyl ethyl ketone and dried in a vacuum desiccator over phosphorous pentoxide to produce crystalline paroxetine methanesulfonate.

The infra-red spectrum and X-ray powder diffractogram were the same as in Example 3.

EXAMPLE 19

Paroxetine methanesulfonate (1.06 g) was added to butan-1-ol (2 ml) and the mixture was heated to reflux temperature while stirring to dissolve, then cooled to 18° C. A white precipitate of needle crystals formed, which was collected by filtration, washed with acetone and dried in vacuo over phosphorous pentoxide to produce crystalline paroxetine methanesulfonate.

The infra-red spectrum and X-ray powder diffractogram were the same as in Example 3.

EXAMPLE 20

Paroxetine methanesulfonate (1.05 g) was added to tetrahydrofuran (9 ml) and the mixture was heated to reflux temperature while stirring to dissolve, then cooled to 18° C. A white precipitate of needle crystals formed, which was collected by filtration, washed with tetrahydrofuran and dried in a vacuum desiccator over phosphorous pentoxide to produce crystalline paroxetine methanesulfonate.

The infra-red spectrum and X-ray powder diffractogram were the same as in Example 3.

EXAMPLE 21

A mixture of paroxetine methanesulfonate (5.0 g) and propan-2-ol (30 ml) was stirred and heated to 70° C. to produce a clear solution. The solution was then cooled at a rate of 2° C. per minute to 55° C. and then seeded with crystals of paroxetine methanesulfonate. The mixture was held at this temperature for 10 minutes and then cooled to 20° C. over a period of 35 minutes. The crystalline solid was collected by filtration, washed with propan-2-ol (10 ml) and dried at 40° C. under vacuum for 2 hours to produce paroxetine methanesulfonate, 4.5 g.

EXAMPLE 22

A mixture of paroxetine methanesulfonate (5.0 g), toluene (55 ml) and acetone (30 ml) was stirred and heated to 75° C. to produce a clear solution. The solution was then cooled to 45° C. over a period of 15 minutes at which point seed crystals of paroxetine methanesulfonate were added. The stirred mixture was held at 45° C. for 10 minutes and was then cooled to 20° C. over a period of 25 minutes. The crystalline solid was collected by filtration, washed with acetone (20 ml) and dried at 40° C. under vacuum for 2 hours to produce paroxetine methanesulfonate, 4.2 g.

EXAMPLE 23

A mixture of paroxetine methanesulfonate (5.0 g) and toluene (30 ml) was stirred and heated to 90° C. to produce a clear solution. The solution was then cooled to 45° C. over a period of 25 minutes. At this point the solution became cloudy and crystallization proceeded rapidly to produce a thick suspension. The cream coloured crystalline solid was collected by filtration, washed with toluene (10 ml) and dried at 40° C. under vacuum for 2 hours to produce paroxetine methanesulfonate, 4.7 g.

EXAMPLE 24

A mixture of paroxetine methanesulfonate (5.0 g), propan-2-ol (30 ml) and water (1 ml) was stirred and heated to reflux to produce a clear solution. The mixture was cooled to 40° C. and was seeded with crystals of paroxetine methanesulfonate. The stirred mixture was then cooled to 21° C. over a period of 40 minutes to produce a thick suspension. The product was collected by filtration, washed with propan-2-ol (10 ml) and dried at 40° C. under vacuum for 2 hours to produce paroxetine methanesulfonate (3.8 g) as a white crystalline solid.

EXAMPLE 25

A solution of paroxetine free base (81.0 g) in toluene (500 ml) was prepared by treating a solution of N-phenoxycarbonyl paroxetine in toluene with potassium hydroxide, followed by washing with water, separation, drying over magnesium sulphate and concentration of the organic layer. Methanesulfonic acid (25.0 g) was added to the stirred solution, under a nitrogen atmosphere, at an initial temperature of 21° C. and the mixture was allowed to rise to 45° C . The mixture was cooled to 21° C. over a period of 30 minutes and stirring continued for a further 30 minutes. The cream coloured crystalline solid was collected by filtration, washed with toluene and dried at 40° C. under vacuum for 1 hour to produce paroxetine methanesulfonate, 104.5 g.

A 90 g portion of this material was recrystallized from propan-2-ol using a computer controlled automated reactor system according to the following procedure:

Paroxetine methanesulfonate (90 g) and propan-2-ol (500 ml) were charged to a computer controlled 1-liter reactor equipped with a thermostatic jacket, an internal temperature probe and an overhead motor driven agitator. The reactor was programmed to use the external thermostatic jacket to enable specific control of the internal reaction temperature over a given period of time. The mixture was stirred at a rate of 100 rpm and heated to 70° C. over a period of 50 minutes and maintained at that temperature for 10 minutes to produce a clear solution. The solution was then stirred and cooled at a rate of 1° C. per minute for 25 minutes at which point seed crystals were added. The stirred mixture was then cooled at a rate of 1° C. per minute for a further 25 minutes. The resulting suspension was drained from the reactor and the solid isolated by vacuum filtration. The filter cake was washed with propan-2-ol (100 ml) and the product dried at 40° C. under vacuum for 2 hours to produce paroxetine methanesulfonate as a white crystalline solid, 82.8 g.

EXAMPLE 26

Paroxetine methanesulfonate (2.47 g) was dissolved in acetonitrile (10 ml), and the solution was brought to reflux temperature with vigorous stirring. The solution was subsequently cooled to −78° C. After a short period crystallisation occurred at the bottom of the flask. After a further half-hour, the product was collected by filtration and dried in a vacuum desiccator over phosphorous pentoxide. The following data indicated that the product formed was crystalline paroxetine methanesulfonate acetonitrile solvate.

Yield=2.58 g.

Molar ratio of paroxetine to methanesulfonic acid=1:1.

Acetonitrile content (estimated by NMR) 8.5% wt/wt.

IR (attenuated total reflectance):

Bands at inter alia 2550, 1624, 1606, 1512, 1488, 1471, 1418, 1377, 1335, 1270, 1207, 1180, 1159, 1141, 1098, 1076, 1039, 1028, 1011, 987, 968, 951, 922, 867, 844, 774, 719, 670, 613, 579 cm$^{-1}$.

IR (nujol mull):

Bands at inter alia 2549, 2247, 1623, 1514, 1489, 1470, 1418, 1377, 1336, 1270, 1209, 1182, 1162, 1098, 1042, 1028, 1012, 987, 922, 845, 832, 813, 792, 776, 720, 671, 614, 580, 552, 537, 524 cm$^{-1}$.

X-ray powder diffractogram major peaks (Cu K$_{2\alpha}$):

| Angle [2θ] | Rel. Int [%] |
|---|---|
| 6.4 | 5.0 |
| 7.8 | 0.6 |
| 9.6 | 9.2 |
| 12.1 | 1.2 |
| 13.0 | 45.8 |
| 14.5 | 5.1 |
| 14.8 | 10.7 |
| 15.9 | 8.9 |
| 17.4 | 5.3 |
| 18.1 | 3.6 |
| 19.6 | 81.1 |
| 20.2 | 13.0 |
| 20.9 | 100.0 |
| 21.9 | 11.3 |
| 23.2 | 19.3 |
| 24.0 | 28.9 |
| 24.4 | 5.5 |
| 25.2 | 12.5 |
| 26.2 | 13.6 |
| 27.0 | 15.2 |
| 27.2 | 16.9 |
| 28.1 | 3.5 |
| 29.4 | 3.2 |
| 30.0 | 8.9 |
| 30.5 | 30.8 |
| 31.7 | 9.4 |
| 32.2 | 4.7 |
| 32.9 | 15.1 |
| 33.8 | 3.2 |
| 34.2 | 4.8 |

EXAMPLE 27

Paroxetine methanesulfonate (6.37 g) was dissolved in acetonitrile (70 ml), and the solution was brought to reflux temperature with vigorous stirring. The solution was subsequently cooled to 45° C. After 1 hour the clear solution was seeded with paroxetine methanesulfonate seeds obtained in Example 26, and treated with ultrasound. During insonation, rapid crystallisation took place. The resulting precipitate was further diluted with acetonitrile (100 ml) and after a further half hour of standing at 45° C., paroxetine methanesulfonate acetonitrile solvate was collected by filtration, washed with acetonitrile and dried in a vacuum desiccator over phosphorous pentoxide.

Yield=7.3 g.

IR and X-ray powder diffraction patterns similar to those obtained in Example 26.

Molar ratio of paroxetine to methanesulfonic acid=1:1.

Acetonitrile content (estimated by NMR) 7.9% wt/wt.

A small sample was placed in a vacuum desiccator over a period of 24 hours. NMR analysis of the resulting product indicated the presence of 6.4% acetonitrile.

DSC (open pan): rate of heating 10.0° C./min, paroxetine methanesulfonate acetonitrile solvate 2.036 mg.

endotherm peak maximum at 77.8° C.
exotherm peak maximum at 85.0° C.
endotherm peak maximum at 92.8° C.
endotherm peak maximum at 148.50° C.

DSC (closed pan): rate of heating 10.0° C./min, paroxetine methanesulfonate acetonitrile solvate 2.315 mg.

endotherm peak maximum at 68.0° C.
exotherm peak maximum at 85° C.
endotherm peak maximum at 92.1° C.
endotherm peak maximum at 134.7° C.
endotherm peak maximum at 148.8° C.

EXAMPLE 28

Paroxetine methanesulfonate (2.22 g) was dissolved in acetonitrile (25 ml) and the solution was brought to reflux temperature with stirring. The solution was subsequently cooled to 45° C. and seeded with paroxetine methanesulfonate seeds obtained in Example 26. After 2 hours the solution was cooled to 18° C. and after a further short period the clear solution began to crystallise. Paroxetine methanesulfonate acetonitrile solvate was collected by filtration in an inert atmosphere, washed with acetonitrile and dried in a vacuum desiccator over phosphorous pentoxide.

Yield=2.6 g.

Molar ratio of paroxetine to methanesulfonic acid=1:1.

Acetonitrile content (estimated by NMR) 7.4% wt/wt.

IR and X-ray powder diffraction patterns similar to those obtained in example 26.

EXAMPLE 29

A round-bottomed flask was charged with a solution of paroxetine base (10.37 g) in toluene (24 ml). The toluene was removed at reduced pressure to produce an oily residue. The residue was diluted with acetonitrile (150 ml) and the solution was heated to reflux temperature. Seed crystals of paroxetine methanesulfonate acetonitrile solvate were added, followed by the dropwise addition of methanesulfonic acid (2.1 ml). The temperature of the solution was cooled to 45° C. and the mixtures insonated for 5 minutes. Crystallisation occurred and the contents of the flask were further diluted with acetonitrile (100 ml). Paroxetine methanesulfonate acetonitrile solvate was collected by filtration under an argon atmosphere, washed with acetonitrile and dried in a vacuum desiccator containing phosphorus pentoxide to produce a white crystalline solid.

Yield 11.3 g.

Molar ratio of paroxetine to methanesulfonic acid=1:1.

Acetonitrile content (estimated by NMR) 10.2% wt/wt.

A small sample was placed in a vacuum desiccator over a period of 24 hours. NMR analysis of the resulting product indicated the presence of 8.0% acetonitrile.

EXAMPLE 30

Paroxetine methanesulfonate (3.61 g) was dissolved in acetonitrile (10 ml), and the solution was brought to reflux temperature with vigorous stirring. The solution was subsequently cooled to 0° C. After a short period the clear solution was seeded with paroxetine methanesulfonate seeds obtained in Example 26. A crystalline precipitate of paroxetine methanesulfonate acetonitrile solvate formed rapidly, and was collected by filtration in an argon atmosphere, washed with acetonitrile and dried in a vacuum desiccator over phosphorous pentoxide.

Yield=4.1 g.

Molar ratio of paroxetine to methanesulfonic acid=1:1.

Acetonitrile content (estimated by NMR) 9.4% wt/wt.

IR and X-ray powder diffraction patterns similar to those obtained in example 26.

EXAMPLE 31

A solution of unpurified paroxetine free base (162 g) in toluene (1.0 liter) was charged to a nitrogen purged reactor, stirred at 20.5° C., and the pale straw coloured mixture seeded with crystals of paroxetine methanesulfonate. A solution of methanesulfonic acid (50.0 g) in propan-2-ol (250 ml) was introduced in a fine stream with good agitation over a period of 5 minutes, giving a reaction temperature of 32.9° C. The mixture was cooled to 25° C. over 1.5 hours, during which the bulk of the product crystallised in a controlled manner. The mixture was further cooled to 21° C., and the dense white crystalline product filtered, and washed with propan-2-ol (250+100 ml) and dried as described below.

The solvent-wet cake (262 g) was placed in a Pro-C-epT Mini-Microwave-Processor equipped with a condenser, and purged with nitrogen. The chamber temperature was set to 25° C., the cake agitated at 25 rpm, and microwave radiation was applied at 100 watts at 100 mbar pressure. The temperature of the product rose to 32° C., and solvent was collected in the receiver at a steady rate. After 30 minutes the product temperature had risen to 35° C. and solvent condensation had ceased, indicating that drying was complete. This was confirmed by the application of full vacuum to the system, which resulted in no drop in the temperature of the product. A total of 72 g of solvent was collected.

Analysis of the white crystalline product by NMR showed that the residual propan-2-ol level was less than 0.1% wt/wt, and analysis by X-ray powder diffraction save a diffractogram which was the same as that for Example 3. Analysis by HPLC showed that the product was very pure (99.45% PAR), with a very significant improvement in the impurity profile over the free base used in the preparation of the methanesulfonate salt:

Impurity profile by PAR (peak area ratio).

| HPLC peak | Free base | Paroxetine methanesulfonate |
| --- | --- | --- |
| peak 1 | 0.03% | 0.00% |
| peak 2 | 0.07 | 0.00 |
| peak 3 | 0.05 | 0.00 |
| peak 4 | 0.02 | 0.01 |
| peak 5 | 0.01 | 0.01 |
| peak 6 | 0.18 | 0.17 |
| peak 7 | 0.10 | 0.09 |
| peak 8 | 0.11 | 0.12 |
| peak 9 paroxetine | 93.48 | 99.45 |
| peak 10 | 0.07 | 0.04 |
| peak 11 | 0.01 | 0.00 |
| peak 12 | 0.04 | 0.01 |
| peak 13 | 0.04 | 0.04 |
| peak 14 | 0.06 | 0.00 |
| peak 15 | 0.12 | 0.00 |
| peak 16 | 0.03 | 0.01 |
| peak 17 | 0.01 | 0.00 |
| peak 18 | 0.11 | 0.01 |
| peak 19 | 0.03 | 0.02 |
| peak 20 | 0.02 | 0.00 |
| peak 21 | 0.01 | 0.00 |
| peak 22 | 5.32 | 0.01 |
| peak 23 | 0.02 | 0.00 |
| peak 24 | 0.02 | 0.00 |
| peak 25 | 0.01 | 0.00 |
| peak 26 | 0.01 | 0.00 |

EXAMPLE 32

Paroxetine methanesulfonate (4.72 g) was added to water (4 ml) with stirring and the mixture was heated to reflux temperature. The resulting solution was cooled to 18° C. and after evaporation of some solvent slowly crystallised to give an off-white precipitate. After 8 days the precipitate was collected by filtration under an argon atmosphere and dried in a vacuum desiccator over phosphorous pentoxide to yield crystalline paroxetine methanesulfonate.

Yield=1.9 g.

X-ray powder diffractogram consistent with Example 3.

EXAMPLE 33

Paroxetine methanesulfonate (2.59 g) was added to a mixture of acetonitrile (24 ml) and water (1 ml) and the mixture was heated to reflux temperature with stirring. On cooling the solution a white precipitate formed, which was collected by filtration, washed with acetonitrile and dried in a desiccator over phosphorous pentoxide to give crystalline paroxetine methanesulfonate acetonitrile solvate.

Yield=1.5 g.

Molar ratio of paroxetine to methane sulfonic acid=1:1.

IR attenuated total reflection:

Bands at 2549, 1622, 1514, 1487, 1471, 1417, 1377, 1336, 1270, 1207, 1180, 1160, 1142, 1098, 1077, 1040, 1027, 1011, 987, 921, 867, 844, 830, 792, 774, 718, 670, 613, 579 cm$^{-1}$.

EXAMPLE 34

Paroxetine methanesulfonate (2.89 g) was added, with stirring, to acetonitrile containing 1% water (25 ml), and the mixture was heated to reflux temperature. The resulting solution was cooled to room temperature (18° C.) whereupon a white solid precipitated. The precipitate was collected by filtration, washed with acetonitrile and dried in a desiccator over phosphorous pentoxide to yield crystalline paroxetine methanesulfonate acetonitrile solvate.

Yield=2.1 g.

Molar ratio of paroxetine to methane sulfonic acid=1:1.

IR attenuated total reflection: Bands at 2548, 1623, 1513, 1487, 1471, 1418, 1377, 1336, 1270, 1207, 1180, 1159, 1142, 1098, 1040, 1027, 1011, 987, 921, 867, 845, 831, 791, 774, 718, 670, 613 cm$^{-1}$.

EXAMPLE 35

Paroxetine base (11.74 g), which had been obtained from the hydrolysis of the phenyl carbamate precursor, was stirred in ethylacetate (50 ml) and the mixture was gently heated to ensure total dissolution. The hot solution was cooled to 35° C., then methanesulfonic acid (2.3 ml) was added dropwise. The solution was cooled, extracted with water (3×70 ml), and the aqueous extracts combined. Most of the water was removed by evaporation under reduced pressure, then toluene was added and the evaporation repeated to remove residual water as an azeotrope. The oily residue was dissolved in propan-2-ol (20 ml), heated to reflux temperature to dissolve, then cooled to give a white precipitate. This precipitate was collected by filtration, washed with propan-2-ol and dried in a vacuum desiccator over phosphorus pentoxide to yield crystalline paroxetine methanesulfonate.

Yield=10.3 g.

EXAMPLE 36

A round bottomed flask was charged with a solution of paroxetine base (8.6 g) in toluene (100 ml), which had been obtained from the hydrolysis of the phenyl carbamate precursor, and methanesulfonic acid (1.86 ml) was added dropwise. The resulting clear solution was placed into a separating funnel, and extracted with water (3×100 ml). The aqueous extracts were combined and evaporated under reduced pressure, then toluene was added and the evaporation repeated to remove residual water as an azeotrope, to produce a crisp solid. The solid was dissolved in toluene (60 ml) by heating to 70° C. and maintained at that temperature. After 3 hours the precipitate that had formed was collected by filtration under an atmosphere of nitrogen, washed with toluene and dried in a vacuum desiccator over phosphorus pentoxide to yield crystalline paroxetine methanesulfonate.

Yield=7.1 g.

EXAMPLE 37

A mixture of the N-benzyl derivative of paroxetine methanesulfonate (3.0 g), 10% palladium on carbon catalyst (150 mg) and propan-2-ol (60 ml) was stirred under an atmosphere of hydrogen (pressure 1 atm) at 60° C. for 5.5 hours. The warm mixture was filtered through celite and the filter cake washed with propan-2-ol (30 ml). The volume of the filtrate was reduced to 20 ml by evaporation under reduced pressure and the solution was stirred at 21° C. under a nitrogen atmosphere for 1 hour. A white crystalline product formed and was collected by filtration, washed with cold propan-2-ol (2×5 ml) and dried at 40° C. under vacuum for 2 hours to give paroxetine methanesulfonate, 1.85 g (75%).

EXAMPLE 38

Methanesulfonic acid (2.5 ml) in propan-2-ol (30 ml) was added dropwise to a stirred solution of paroxetine acetate (13.6 g) in propan-2-ol (130 ml) at 50° C. The solution was cooled to 40° C., seeded with crystalline paroxetine methanesulfonate, sonicated and stirred for one hour while the product crystallised. The resulting solid was collected by filtration, washed with propan-2-ol (50 ml), and dried over phosphorus pentoxide in a vacuum desiccator to give crystalline paroxetine methanesulfonate as a crystalline white solid.

Yield=15.1 g.

EXAMPLE 39

Paroxetine maleate form B (1.89 g) was dissolved in warm propan-2-ol (50 ml) and a solution of methanesulfonic acid (0.29 ml) in propan-2-ol (10 ml) was added. The solution was brought to reflux temperature, cooled to 30° C., seeded with crystalline paroxetine methanesulfonate and sonicated. Crystallisation rapidly occurred. The thick suspension was diluted with propan-2-ol (20 ml), and the precipitate was collected by filtration, washed with propan-2-ol (30 ml) and dried over phosphorus pentoxide in a vacuum desiccator to yield crystalline paroxetine methanesulfonate.

Yield=1.4 g.

EXAMPLE 40

Methanesulfonic acid (0.4 ml) in propan-2-ol (10 ml) was added dropwise to a stirred solution of paroxetine maleate form A (2.95 g) in propan-2-ol (40 ml). The reaction was brought to reflux temperature, cooled to 30° C. seeded with crystalline paroxetine methanesulfonate, and sonicated.

Crystallisation rapidly occurred. The crystals of paroxetine methanesulfonate were collected by filtration, washed with propan-2-ol (40 ml) and dried over phosphorus pentoxide in a vacuum desiccator.

Yield=2.1 g.

EXAMPLE 41

Paroxetine L(+) tartrate (18.5 g) was added to propan-2-ol (150 ml) and water (20 ml) and the mixture was brought to reflux temperature with stirring to ensure total dissolution. The solution was cooled to 50° C. and methanesulfonic acid (2.8 ml) in propan-2-ol (10 ml) was added. Propan-2-ol (60 ml) was added and solvent (170 ml) was removed by distillation. The clear yellow solution was seeded with crystalline paroxetine methanesulfonate, sonicated, cooled to 0–5° C. and a white precipitate formed. The solid was collected by filtration, washed with propan-2-ol (40 ml) and dried to yield crystalline paroxetine methanesulfonate.

Yield=4.4 g.

EXAMPLE 42

Methanesulfonic acid (0.6 ml) in propan-2-ol (25 ml) was added dropwise to a stirred solution of paroxetine L(+) tartrate (4.99 g) in water (25 ml) at 50° C. After 1 hour, the solvents were removed at reduced pressure to afford a crisp solid. Propan-2-ol (25 ml) was added and the mixture was heated to reflux temperature, seeded with crystalline paroxetine methanesulfonate and cooled to 0–5° C. to afford a white precipitate. The precipitate was collected by filtration washed with propan-2-ol (30 ml) and dried in a vacuum desiccator to give crystalline paroxetine methanesulfonate.

Yield=1.9 g.

EXAMPLE 43

A round bottom flask was charged with unpurified paroxetine base (8.6 g) in toluene (20 ml) which had been prepared by potassium hydroxide hydrolysis of a phenylcarbamate derivative, and a solution of methanesulfonic acid (1.9 ml) in toluene (10 ml) was added dropwise. The resulting clear solution was placed into a separating funnel and extracted with water (30 ml). The aqueous phase was separated, residual toluene removed by evaporation at reduced pressure and the remaining clear solution (25 ml) was further diluted with water (40 ml). The water was removed by freeze drying to afford amorphous paroxetine methanesulfonate.

Yield=9.1 g.

Infra-red (attenuated total reflection).

Bands at: 1605, 1510, 1503, 1488,1470, 1394, 1335, 1269, 1219, 1178, 1158, 1098,1034, 928, 831, 799, 773, 653, 612, 593, 579, 569 cm$^{-1}$.

EXAMPLE 44

Methanesulfonic acid (1.86 ml) in toluene (15 ml) was added dropwise to a stirred solution of unpurified paroxetine base (8.6 g) in toluene (20 ml) which had been prepared by potassium hydroxide hydrolysis of a phenylcarbamate derivative. The clear solution was placed into a separating funnel and extracted with water (15 ml). The aqueous phase was separated and the water removed by evaporation at reduced pressure. Propan-2-ol (50 ml) was added, and residual water was removed by evaporation at reduced pressure as an azeotrope with propan-2-ol. The remaining solution (40 ml) was heated to 40° C. and stirred while the product crystallised. The resulting paroxetine methanesulfonate was collected by filtration, washed with propan-2-ol (20 ml) and dried over phosphorus pentoxide in a vacuum desiccator.

Yield=9.1 g.

EXAMPLE 45

Methanesulfonic acid (2.1 ml) in propan-2-ol (10 ml) was added dropwise to a stirred solution of paroxetine base (11.92 g) in propan-2-ol (30 ml). The resulting clear solution was heated to 50° C. and hexane (200 ml) containing seed crystals of paroxetine methanesulfonate was added in small volumes. The solution was vigorously stirred at approximately 50° C. for 30 minutes to crystallise. The resulting white solid was collected by filtration washed with hexane (50 ml) and dried in a vacuum desiccator over phosphorus pentoxide to produce crystalline paroxetine methanesulfonate.

Yield=3.02 g.

EXAMPLE 46

To a stirred solution of paroxetine base (20.9 g) in propan-2-ol (70 ml) was added methanesulfonic acid (3.7 ml) in propan-2-ol (10 ml). The solution was heated to 50° C. and added portion-wise to hexane (200 ml) also at 50° C. The solution was stirred vigorously to form a precipitate which was stirred further to ensure crystallisation. The precipitate was collected by filtration, washed with hexane (40 ml) and dried in a vacuum desiccator over phosphorus pentoxide to give paroxetine methanesulfonate as a white crystalline solid.

Yield=23.1 g.

EXAMPLE 47

Amberlite 'IRA'-93(OH) (78 g) was slurried in water and poured into a column (10 cm×4.5 cm). The eluting solvent was gradually changed from water to methanol, and the column was repacked. The resin was converted to the methanesulfonate form by eluting with methanesulfonic acid (2.2 ml) in methanol (50 ml), and excess acid was washed off the column with methanol (300 ml). A solution of paroxetine hydrochloride (6.9 g) in methanol (50 ml) was loaded onto the column and eluted through with methanol (350 ml) over 1 hour. The methanol eluent was evaporated at reduced pressure to an oil. Propan-2-ol (100 ml) was added and the mixture was heated to 60° C., seeded with crystalline paroxetine methanesulfonate and cooled to room temperature (18° C.). The resulting white precipitate was collected by filtration, washed with propan-2-ol (20 ml) and dried in a vacuum desiccator over phosphorus pentoxide to give paroxetine methanesulfonate as a white crystalline solid.

Yield=6.6 g.

EXAMPLE 48

Amberlite IRA-93(OH) resin (basic form) (146 g) was slurried in water and poured into a column (16.5 cm×4.5 cm). The eluting solvent was gradually changed from water to water/methanol (1:1) and the column was repacked. The resin was converted to the methanesulfonate form by eluting with methanesulfonic acid (10 ml) in methanol/water (1:1) (20 ml), and excess acid was washed off the column with methanol/water (1:1) (350 ml). A solution of paroxetine hydrochloride (12.86 g) in methanol/water (1:1) (50 ml) was loaded onto the column and eluted with methanol:water (1:1) (350 ml) over 1 hour. The eluent was evaporated at reduced pressure to give a crisp solid. Propan-2-ol (120 ml) was added and the mixture was heated to reflux temperature and cooled to 40° C. The resulting white precipitate was collected by filtration, washed with propan-2-ol (50 ml) and dried in a vacuum desiccator over phosphorus pentoxide to give paroxetine methanesulfonate as a white crystalline solid.

Yield=14.8 g.

EXAMPLE 49

Methanesulfonic acid (1.00 ml) was added to a solution of (3S,4R)-3-(Benzo[1,3] dioxol-5-yloxymethyl)-4-(4-fluorophenyl)piperidine-1-carboxylic acid tertbutyl ester (3.30 g) in propan-2-ol. The reaction mixture was stirred at 22° C. under nitrogen for 4 hours then the reaction mixture was concentrated to approximately 20 ml, seeds of paroxetine methanesulfonate salt added (approximately 20 mg) and the solution left to crystallise. After standing for 19 hours at 22–23° C., needle crystals of paroxetine methanesulfonate were collected by filtration, washed with propan-2-ol and dried under vacuum. A second crop of paroxetine methanesulfonate was collected from the filtrate after standing at 23° C. for 6 hours.

EXAMPLE 50

A solution of (Benzo[1,3]dioxol-5-yloxymethyl)-4-(4-fluorophenyl)piperidine-1-carboxylic acid tert-butyl ester (4.10 g) in dichloromethane was treated with a solution of methanesulfonic acid (0.97 g) in dioxane (20 ml) at 22° C. The reaction mixture was stirred at this temperature for 48 hours, then methanesulfonic acid (1 ml) was added and the reaction mixture heated at reflux for 5 hours. The mixture was cooled to room temperature (22° C.) and left to stand for 22 hours, then evaporated to approximately 10 ml under reduced pressure. Propan-2-ol was added (60 ml) and the solution seeded with paroxetine methanesulfonate (20 mg) and stirred at room temperature for 1 hour. Paroxetine methane sulfonate was isolated by filtration, washed with cold propan-2-ol (5 ml) and dried under vacuum. Yield 2.38 g.

EXAMPLE 51

Aqueous hydrochloric acid (0.48M, 25.0 ml) was added to a stirred solution of paroxetine methanesulfonate (5.0 g) in water (50 ml) at 40° C. over a period of 15 minutes. The resulting thick white suspension was stirred and cooled to 20° C. The product was collected by filtration, washed with water (20 ml) and dried at 40° C. under vacuum over phosphorus pentoxide for 2 hours to give crystalline paroxetine hydrochloride hemihydrate, 3.9 g. The infra-red spectrum obtained was consistent with that of crystalline paroxetine hydrochloride hemihydrate.

EXAMPLE 52

Paroxetine methanesulfonate was added portionwise over a period of 5 minutes to dilute aqueous hydrochloric acid (0.172M, 75 ml) at 21° C. A precipitate formed quickly, but the mixture was stirred for 30 minutes to ensure complete crystallisation. The product was collected by filtration washed with water (20 ml) and dried at 40° C. under vacuum over phosphorus pentoxide for 2 hours to give crystalline paroxetine hydrochloride hemihydrate, 4.0 g. The infra-red spectrum obtained was consistent with that obtained for crystalline paroxetine hydrochloride hemihydrate.

EXAMPLE 53

A solution of paroxetine methanesulfonate (5.0 g) in water (20 ml) was added to dilute hydrochloric acid (0.10M, 125 ml) at 40° C. with stirring over a period of 10 minutes. The resulting suspension was stirred and cooled to 20° C. and the product was collected by filtration. The filter cake was washed with water (30 ml) and the product dried at 40° C. under vacuum over phosphorus pentoxide for 2 hours to give crystalline paroxetine hydrochloride hemihydrate, 3.1 g. The infra-red spectrum obtained was consistent with that obtained for crystalline paroxetine hydrochloride hemihydrate.

EXAMPLE 54

| INGREDIENTS | 20 mg Tablet | 30 mg Tablet |
|---|---|---|
| Paroxetine Methanesulfonate | 20.00 mg (calc. as free base) | 30.0 mg (calc. as free base) |
| Dicalcium Phosphate (DCP) | 83.34 mg | 125.0 mg |
| Microcrystalline Cellulose | 50.67 mg | 76.0 mg |
| Sodium Starch Glycollate | 8.34 mg | 12.5 mg |
| Magnesium Stearate | 1.67 mg | 2.5 mg |

Commercial Source of the Ingredients
  Dicalcium Phosphate Dihydrate-Emcompress or Ditab*
  Microcrystalline Cellulose-Avicel PH 102*
  Sodium Starch Glycollate-Explotab.*
* Trade names
Method
  1. Pass DCP through a screen and weigh it into a Planetary mixer.
  2. Add 30 mesh Paroxetine Methanesulfonate to the bowl.
  3. Add 20 mesh Avicel and Explotab and mix all the powders for 10 minutes.
  4. Add magnesium stearate and mix for 5 minutes.
Tablet into Pentagonal Tablets using the following punches:

| 30 mg Tablet | 9.5 mm | Circumcircle |
|---|---|---|
| 20 mg Tablet | 8.25 mm | Circumcircle |

The tablets are made satisfactorily on a single punch or a Rotary press.

EXAMPLE 55

| INGREDIENTS | 10 mg Tablet | 20 mg Tablet | 30 mg Tablet |
|---|---|---|---|
| Paroxetine Methanesulfonate | 10 mg (calc. as free base) | 20 mg (calc. as free base) | 30 mg (calc. as free base) |
| Sodium Starch Glycollate | 2.98 mg | 5.95 mg | 8.93 mg |
| Granular Dicalcium Phosphate (DITAB) or Dicafos | 158.88 mg | 317.75 mg | 476.63 mg |
| Magnesium Stearate | 1.75 mg | 3.50 mg | 5.25 mg |

Method

1. Paroxetine Methanesulfonate, Sodium Starch Glycollate and Dicalcium Phosphate Dihydrate are screened and mixed together in a suitable mixer. (Planetary, Cuble or High Energy Shear mixer.)

2. Add Magnesium Stearate and compress it into a tablet using a single punch or Rotary Tablet machine.

We claim:

1. Paroxetine methanesulfonate in crystalline form having the following characteristic IR peaks: 1603, 1194, 1045, 946, 830, 601, 554, and 539±4 cm−1.

2. Paroxetine hydrochloride formed by conversion of paroxetine methanesulfonate, as described in claim 1, by contacting said paroxetine methanesulfonate with hydrochloric acid.

3. Paroxetine methanesulfonate in crystalline form having the following characteristic IR peaks: 1603, 1194, 1045, 946, 830, 601, 554, and 539 cm−1.

4. Paroxetine hydrochloride formed by conversion of paroxetine methanesulfonate, as described in claim 1, by contacting said paroxetine methanesulfonate with hydrochloric acid.

* * * * *

UNITED STATES PATENT AND TRADEMARK OFFICE
CERTIFICATE OF CORRECTION

PATENT NO. : 6,063,927
DATED : May 16, 2000
INVENTOR(S) : Craig et al.

It is certified that error appears in the above-indentified patent and that said Letters Patent is hereby corrected as shown below:

On the cover page; in the list of inventors, delete "Alan David Jones, both of Kent; Deirdre O'Keeffe, Surrey; Neal Ward, East Sussex," and replace with --- Victor Witold Jacewicz and Michael Urquhart, all of Kent, ---.

In claim 4, column 26, line 34:
change ", as described in claim 1," to --- , as described in claim 3, ---.

Signed and Sealed this

Third Day of April, 2001

Attest:

NICHOLAS P. GODICI

*Attesting Officer*     *Acting Director of the United States Patent and Trademark Office*